United States Patent
Ilekti et al.

(10) Patent No.: US 9,968,544 B2
(45) Date of Patent: May 15, 2018

(54) COSMETIC COMPOSITION FOR COATING KERATIN FIBRES

(71) Applicant: L'OREAL, Paris (FR)

(72) Inventors: Philippe Ilekti, Maisons-Alfort (FR); Zohra Moujahed, Savigny-sur-Orge (FR)

(73) Assignee: L'OREAL, Paris (FR)

( * ) Notice: Subject to any disclaimer, the term of this patent is extended or adjusted under 35 U.S.C. 154(b) by 0 days. days.

(21) Appl. No.: 14/363,007

(22) PCT Filed: Nov. 30, 2012

(86) PCT No.: PCT/EP2012/074089
§ 371 (c)(1),
(2) Date: Jun. 5, 2014

(87) PCT Pub. No.: WO2013/087426
PCT Pub. Date: Jun. 20, 2013

(65) Prior Publication Data
US 2014/0328785 A1 Nov. 6, 2014

Related U.S. Application Data

(60) Provisional application No. 61/577,108, filed on Dec. 19, 2011.

(30) Foreign Application Priority Data

Dec. 14, 2011 (FR) .................... 11 61590

(51) Int. Cl.
A61Q 1/10 (2006.01)
A61K 8/31 (2006.01)
A61K 8/92 (2006.01)
A61K 8/44 (2006.01)
A61K 8/55 (2006.01)
A61K 8/73 (2006.01)
A61K 8/06 (2006.01)
A61K 8/37 (2006.01)

(52) U.S. Cl.
CPC .................. *A61K 8/92* (2013.01); *A61K 8/06* (2013.01); *A61K 8/31* (2013.01); *A61K 8/37* (2013.01); *A61K 8/44* (2013.01); *A61K 8/55* (2013.01); *A61K 8/73* (2013.01); *A61K 8/731* (2013.01); *A61K 8/922* (2013.01); *A61K 8/927* (2013.01); *A61Q 1/10* (2013.01); *A61K 2800/49* (2013.01); *A61K 2800/52* (2013.01); *A61K 2800/596* (2013.01)

(58) Field of Classification Search
CPC .............. A61Q 1/10; A61K 8/44; A61K 8/06
See application file for complete search history.

(56) References Cited

U.S. PATENT DOCUMENTS

| | | | |
|---|---|---|---|
| 2006/0193807 A1* | 8/2006 | Lezer et al. | 424/70.13 |
| 2008/0124292 A1 | 5/2008 | Collin et al. | |
| 2009/0142289 A1 | 6/2009 | Arditty et al. | |
| 2010/0119467 A1* | 5/2010 | Dumousseaux et al. | 424/70.7 |
| 2010/0278770 A1 | 11/2010 | Arditty et al. | |

FOREIGN PATENT DOCUMENTS

| | | |
|---|---|---|
| EP | 1 920 760 A1 | 5/2008 |
| EP | 2 030 609 A2 | 3/2009 |
| EP | 2 248 508 A2 | 11/2010 |
| FR | 2 954 115 A1 | 6/2011 |

OTHER PUBLICATIONS

"Paraffin", "Carnauba Wax", "Beeswax", The Merck Index Online, 2013, Royal Society of Chemistry.*
International Search Report dated Jan. 4, 2013 in PCT/EP2012/074089.
L'Oreal: "L'Oreal Lash Architect 4D", Database GNPD Mintel, XP002681798, Nov. 1, 2011, 2 Pages.
U.S. Appl. No. 14/363,059, filed Jun. 5, 2014, Ilekti, et al.
U.S. Appl. No. 14/433,761, filed Apr. 6, 2015, Ilekti, et al.
U.S. Appl. No. 14/432,369, filed Mar. 30, 2015, Ilekti.
U.S. Appl. No. 14/432,011, filed Mar. 27, 2015, Ilekti, et al.
U.S. Appl. No. 14/431,937, filed Mar. 27, 2015, Ilekti, et al.
U.S. Appl. No. 14/432,059, filed Mar. 27, 2015, Ilekti, et al.

* cited by examiner

*Primary Examiner* — Gina C Justice
(74) *Attorney, Agent, or Firm* — Oblon, McClelland, Maier & Neustadt, L.L.P.

(57) ABSTRACT

The present invention relates to a cosmetic composition for coating keratin fibres of the emulsion type, comprising: an aqueous phase, at least one wax, an emulsifying system comprising: i) at least one $C_{12}$-$C_{22}$ monoalkylphosphate, ii) at least one acyl glutamic acid having at least one $C_{12}$-$C_{22}$ acyl chain, their salt(s), and their mixture(s). The present invention also relates to a method for coating keratin fibres.

18 Claims, No Drawings

COSMETIC COMPOSITION FOR COATING KERATIN FIBRES

The present invention relates to a cosmetic composition for coating keratin fibres, and especially eyelashes or eyebrows. In particular, said cosmetic composition is a composition for making up and optionally caring for eyelashes. The present invention also relates to a method for coating keratin fibres, especially a method for making up and optionally caring for eyelashes.

The composition used may especially be in the form of an eyelash product such as a mascara, or an eyebrow product. More preferentially, the invention relates to a mascara. The term "mascara" means a composition intended to be applied to the eyelashes: it may be an eyelash make-up composition, an eyelash make-up base (also known as a base coat), a composition to be applied over a mascara, also known as a top coat, or a cosmetic composition for treating the eyelashes. The mascara is more particularly intended for human eyelashes, but also false eyelashes.

Mascaras are especially prepared according to two types of formulation: water-based mascaras known as cream mascaras, in the form of a dispersion of waxes in water; anhydrous mascaras or mascaras with a low water content, known as waterproof mascaras, in the form of dispersions of waxes in organic solvents. The present patent application more specifically relates to water-based mascaras.

Keratin fibre coating compositions of such a mascara type generally consist of at least one fatty phase generally formed from one or more waxes dispersed in an aqueous liquid phase by means of an emulsifying system or conveyed in an organic solvent.

The application of mascara is especially directed towards increasing the volume of the eyelashes and consequently increasing the intensity of the gaze. Numerous thickening or volumizing mascaras exist to do this, whose principle consists in depositing a maximum amount of material onto the eyelashes so as to obtain this volumizing (or charging) effect. It is especially by means of the amount of solid particles that the desired application specificities for compositions may be adjusted, for instance their fluidity or consistency, and also their thickening power (also known as the charging or make-up power). These solid particles are dispersed in the cream mascara by means of an emulsifying system composed of one or more surfactant(s).

However, a specific problem found with some surfactants, especially ionic surfactants, is that they are generally unstable at low temperature (4° C.), so they crystallize and destabilize the emulsion, leading to substances (waxes especially) aggregating on the eyelashes.

A more specific aim of the present application is to propose a stable mascara with a sufficiently thick texture to deliver a charging deposit, with satisfactory consistency, that can be applied easily to eyelashes with a regular deposit, i.e. smooth and even, even after being stored for two months at 4° C.

An aim of the present application is also to propose a stable mascara with a sufficiently thick texture to deliver a charging deposit, with satisfactory consistency, that can be applied easily to eyelashes with a regular deposit, i.e. smooth and even, even after being stored for two months at 45° C.

A more specific aim of the present application is to propose a stable mascara with a sufficiently thick texture to deliver a charging deposit, with satisfactory consistency, that can be applied easily to eyelashes with a regular deposit, i.e. smooth and even, even after being stored for two months at temperatures varying between 4° C. and 45° C.

An aim of the present application is more specifically to propose a mascara in which the waxes are dispersed evenly.

An aim of the present application is more specifically to propose a mascara in which the pigments are dispersed evenly.

An aim of the present application is more specifically to propose a mascara that is pleasant to apply.

An aim of the present invention is more specifically to propose a composition for coating keratin fibres that allows good separation of the eyelashes during its application, without formation of bunches of eyelashes, while ensuring smooth and uniform deposition of material (without lumps of composition).

An aim of the present invention is more specifically to obtain a composition for coating keratin fibres, preferably a mascara, having good application properties in terms of slip and playtime.

One further aim of the present invention is to obtain a composition for coating keratin fibres, preferably a mascara, which gives rise to a volumizing effect on the eyelashes.

One further aim of the present invention is to obtain a composition for coating keratin fibres, preferably a mascara, having good hold on the eyelashes.

One further aim of the present invention is to obtain a composition for coating keratin fibres, preferably a mascara, which gives rise to a charging or covering deposit.

One further aim of the present invention is to obtain a composition for coating keratin fibres, preferably a mascara, having good lengthening properties for the eyelashes coated with such a composition.

One further aim of the present invention is to obtain a composition for coating keratin fibres, preferably a mascara, having good curling properties for the eyelashes coated with such a composition.

One further aim of the present invention is to obtain a composition for coating keratin fibres, preferably a mascara, having good blackness intensity, as regards both colorimetry and chromaticity.

One further aim of the present invention is to obtain a composition for coating keratin fibres, preferably a mascara, having good adherence to the eyelashes.

Consequently, the present invention relates to a cosmetic composition for coating keratin fibres, preferably the eyelashes, preferably a mascara composition, of the emulsion type, preferably wax(es) in water emulsion type, comprising:
  an aqueous phase,
  at least one wax,
  an emulsifying system comprising:
    i) at least one $C_{12}$-$C_{22}$ monoalkyl phosphate,
    ii) at least one acyl glutamic acid having at least one $C_{12}$-$C_{22}$ acyl chain, their salt(s), and their mixture(s).

In an unexpected and surprising manner, the inventors of the present application have resolved this/these problem(s) using such a composition. Specifically, a composition in accordance with the invention gives rise to a stable composition, with an even and uniform dispersion of waxes, even after two months, whether at 45° C. or at 4° C. It seems that such a composition also has good pigment dispersion. Such a composition is also pleasant to apply.

According to a second aspect, the present invention also relates to an assembly or kit for coating keratin fibres, comprising:
  at least one cosmetic composition for coating keratin fibres as described previously, and at least one applicator for the composition, said applicator comprising means, where appropriate in relief, configured to come into contact with said keratin fibres, such as eyelashes or eyebrows, so as to smooth and/or separate the eyelashes or eyebrows. Such reliefs may comprise teeth, bristles or the like. Said assembly, and especially said applicator, may optionally be equipped with means for vibrating and/or heating said composition.

According to a third aspect, a subject of the present invention is also an assembly or kit for packaging and applying a composition for coating keratin fibres, comprising:
- a device for packaging said cosmetic composition for coating keratin fibres as described previously,
- an applicator for said composition.

Said applicator may be integrally attached to a handling member forming a cap for said packaging device. In other words, said applicator may be mounted in a removable position on said device between a closed position and an open position of a dispensing aperture of the device for packaging said composition.

According to a fourth aspect, the present invention also relates to a method for coating keratin fibres, and especially for making up the eyelashes, comprising a step of applying a cosmetic composition for coating keratin fibres as described previously.

According to particular preferred embodiments of the present invention:
- the emulsion is a wax(es)-in-water type emulsion;
- said composition comprises a fatty phase dispersed in the aqueous phase;
- said composition is free of oil or organic solvent;
- the fatty phase comprises mainly waxes, particularly a mixture of polar wax(es) and non-polar wax(es);
- the total wax content is greater than or equal to 10% by weight relative to the total weight of the composition, preferably comprised between 15% and 40% by weight relative to the total weight of the composition;
- the total non-polar wax content is greater than or equal to 7% by weight relative to the total weight of the composition, preferably inclusively comprised between 10% and 40% by weight relative to the total weight of the composition;
- the non-polar wax(es) is (are) chosen from hydrocarbon waxes, preferably from microcrystalline waxes, paraffin waxes, ozokerite, polyethylene waxes, and their mixture(s);
- the total polar wax content is greater than or equal to 7% by weight relative to the total weight of the composition, preferably comprised between 10% and 40% by weight relative to the total weight of the composition;
- the polar wax(es) is (are) chosen from ester waxes, alcohol waxes, silicone waxes, and their mixture(s);
- said composition comprises at least:
    - one ester wax chosen from among:
        - i) waxes having formula $R_1COOR_2$ in which $R_1$ and $R_2$ denote linear, branched or cyclic aliphatic chains, whose number of atoms varies from 10 to 50, that may contain a heteroatom such as O, N or P and whose melting points vary from 25 to 120° C.;
        - ii) di(1,1,1-trimethylolpropane)tetrastearate;
        - iii) diester waxes of a dicarboxylic acid having general formula $R^3$—(—OCO—$R^4$—COO—$R^5$), in which $R^3$ and $R^5$ are the same or different, preferably the same, and denote a $C_4$-$C_{30}$ alkyl group (alkyl group comprising from 4 to 30 carbon atoms) and $R^4$ denotes a linear or branched $C_4$-$C_{30}$ aliphatic group (alkyl group comprising from 4 to 30 carbon atoms) that may or may not contain one or more unsaturated groups, and that is preferably linear and unsaturated;
        - iv) the waxes obtained by catalytic hydrogenation of animal or vegetable oils having linear or branched $C_8$-$C_{32}$ fatty chains, and waxes obtained by hydrogenation of castor oil esterified with cetyl alcohol, and waxes obtained by hydrogenation of olive oil esterified with alcohol; and
        - v) beeswax, synthetic beeswax, polyglycerolated beeswax, carnauba wax, candelilla wax, oxypropylenated lanolin wax, rice bran wax, ouricury wax, esparto grass wax, cork fibre wax, sugar cane wax, Japan wax, sumach wax; montan wax, orange wax, laurel wax and hydrogenated jojoba wax.
        - vi) and their mixture(s);
    - at least one alcohol wax, and their mixture(s);
    - at least one silicone wax, and their mixture(s);
    - and the mixture of several of these waxes;
- said composition comprises at least one polar wax, preferably at least two polar waxes, chosen from beeswax, synthetic beeswax, polyglycerolated beeswax, carnauba wax, candelilla wax, oxypropylenated lanolin wax, rice bran wax, ouricury wax, esparto grass wax, cork fibre wax, sugar cane wax, Japan wax, sumach wax, montan wax, orange wax, laurel wax and hydrogenated jojoba wax and their mixture(s).
- the total content of non-polar wax(es) and the total content of polar wax(es) are such that the weight ratio of non-polar wax(es) over polar wax(es) is greater than or equal to 1/3;
- said composition comprises at least 20% by weight of non-polar wax(es), preferably at least 40% by weight of non-polar wax(es), relative to the total weight of wax(es);
- the total $C_{12}$-$C_{22}$ monoalkyl phosphate content is greater than or equal to 0.5% by weight relative to the total weight of the composition;
- the total acyl glutamic acid content is greater than or equal to 0.5% by weight relative to the total weight of the composition;
- the total $C_{12}$-$C_{22}$ monoalkyl phosphate content and the total acyl glutamic acid content are such that the weight ratio of $C_{12}$-$C_{22}$ monoalkyl phosphate content and glutamic acid content is inclusively comprised between 1/3 and 3, preferably between 3/5 and 5/3;
- the total $C_{12}$-$C_{22}$ monoalkyl phosphate content plus the total acyl glutamic acid content and the total wax content are such that the weight ratio of $C_{12}$-$C_{22}$ monoalkyl phosphate(s) together with the acyl glutamic acid(s), relative to the wax(es), is greater than or equal to 1/10, preferably comprised between 1/8 and 1/2, more preferably between 1/4 and 1/3;
- said composition comprises at least one hydrophilic and/or lipophilic film-forming polymer, preferably a hydrophilic film-forming polymer;
- said composition may comprise at least one dyestuff chosen from one or more pulverulent dye stuff(s), preferably metal oxides, and especially iron oxides.
- the metal oxide(s) is (are) preferably present in a content of greater than or equal to 2% by weight relative to the total weight of the composition, and advantageously comprised inclusively between 3% and 15% by weight relative to the total weight of the composition;

said composition may be a make-up composition, a make-up base or base coat, a composition called a top coat to be applied over make-up;

said composition has a viscosity at 20° C. comprised between 30 and 300 poises, preferably between 60 and 150 poises. The viscosity measurement is performed at 20° C., using a Rheomat RM180 viscometer equipped with a No. 4 spindle, the measurement being performed after 10 minutes of rotation of the spindle (after which time stabilization of the viscosity and of the spin speed of the spindle are observed), at a shear rate of 200 $s^{-1}$.

Other characteristics, properties and advantages of the present invention will emerge more clearly on reading the description and the examples that follow.

Aqueous Phase

The composition according to the invention comprises an aqueous phase, which may form a continuous phase of the composition.

The aqueous phase comprises water. It may also comprise at least one water-soluble solvent.

In the present invention, the term "water-soluble solvent" denotes a compound that is liquid at room temperature (20° C.) and at atmospheric pressure (760 mmHg) and water-miscible.

The water-soluble solvents that may be used in the compositions according to the invention may also be volatile.

Among the water-soluble solvents that may be used in the compositions in accordance with the invention, mention may be made especially of lower monoalcohols containing from 1 to 5 carbon atoms such as ethanol and isopropanol, and glycols containing from 2 to 8 carbon atoms such as ethylene glycol, propylene glycol, 1,3-butylene glycol and dipropylene glycol.

The aqueous phase (water and optionally the water-miscible solvent) is generally present in the composition according to the present patent application in a content ranging from 20% to 90% by weight, preferably ranging from 25% to 80% by weight, preferentially ranging from 30% to 70% by weight and better still from 45% to 60% by weight relative to the total weight of the composition.

Fatty Phase

A fatty phase in accordance with the invention advantageously comprises at least one wax, chosen from at least one non-polar wax, at least one polar wax, and their mixture(s).

This fatty phase may also comprise constituents chosen especially from at least one volatile oil, at least one additional non-volatile oil, pasty fatty substances and their mixture(s).

Preferably, the fatty phase is constituted largely of waxes and even more preferably exclusively of waxes. According to a preferred embodiment, the fatty phase comprises at least 75% by weight of wax(es), even more preferably at least 90% by weight of waxes, relative to the total weight of the fatty phase.

Wax(es)

The wax(es) under consideration in the context of the present invention is (are) generally a lipophilic compound that is solid at room temperature (20° C.) and at atmospheric pressure (760 mmHg), with a solid/liquid reversible change of state, having a melting point of greater than or equal to 30° C., which may be up to 200° C. and especially up to 120° C.

In particular, the waxes that are suitable for the invention may have a melting point of greater than or equal to 45° C. and in particular of greater than or equal to 55° C.

For the purposes of the invention, the melting point corresponds to the temperature of the most endothermic peak observed on thermal analysis (DSC) as described in standard ISO 11357-3; 1999. The melting point of the wax may be measured using a differential scanning calorimeter (DSC), for example the calorimeter sold under the name DSC Q2000 by TA Instruments.

Preferably, the waxes comprise at least one crystallizable portion, which is visible by X-ray diffraction observation.

Preferably, the waxes have an enthalpy of fusion ΔHf of greater than or equal to 70 J/g.

The measuring protocol is as follows:

A sample of 5 mg of wax placed in a crucible is subjected to a first temperature rise passing from −20° C. to 120° C., at a heating rate of 10° C./minute, it is then cooled from 120° C. to −20° C. at a cooling rate of 10° C./minute and is finally subjected to a second temperature rise passing from −20° C. to 120° C. at a heating rate of 5° C./minute. During the second temperature rise, the following parameters are measured:

the melting point ($T_f$) of the wax, as mentioned previously corresponding to the temperature of the most endothermic peak of the melting curve observed, representing the variation in the difference in power absorbed as a function of the temperature, ΔHf: the enthalpy of fusion of the wax, corresponding to the integral of the entire melting curve obtained. This enthalpy of fusion of the wax is the amount of energy required to make the compound change from the solid state to the liquid state. It is expressed in J/g.

The wax(es) may be hydrocarbon-based waxes, fluoro waxes and/or silicone waxes and may be of plant, mineral, animal and/or synthetic origin.

The wax(es) may be present in a content of greater than or equal to 10% by weight relative to the total weight of the composition, better 12% by weight relative to the total weight of the composition. Preferably, it is (they are) present in a content ranging from 15% to 40% by weight, better from 20% to 35% by weight and better still from 25% to 30% by weight relative to the total weight of the composition.

A composition according to the invention advantageously comprises at least one non-polar wax. Preferably a composition according to the invention comprises at least one non-polar wax and at least one polar wax.

Non-Polar Waxes:

A composition according to the invention comprises advantageously at least one non-polar wax.

For the purposes of the present invention, the term "non-polar wax" means a wax whose solubility parameter $\delta_a$ calculated above its melting point as defined below is equal to 0 $(J/cm^3)^{1/2}$.

The definition and calculation of the solubility parameters in the Hansen three-dimensional solubility space are described in the article by C. M. Hansen: "The three dimensional solubility parameters", J. Paint Technol. 39, 105 (1967).

According to this Hansen space:

$\delta_D$ characterizes the London dispersion forces derived from the formation of dipoles induced during molecular impacts;

$\delta_p$ characterizes the Debye interaction forces between permanent dipoles and also the Keesom interaction forces between induced dipoles and permanent dipoles;

$\delta_h$ characterizes the specific interaction forces (such as hydrogen, acid/base, donor/acceptor bonds, etc.); and $\delta_a$ is determined by the equation: $\delta_a = (\delta_p^2 + \delta_h^2)^{1/2}$ The parameters $\delta_p$, $\delta_h$, $\delta_D$ and $\delta_a$ are expressed in $(J/cm^3)^{1/2}$.

Non-polar waxes are especially hydrocarbon-based waxes constituted solely of carbon and hydrogen atoms, and free of heteroatoms such as N, O, Si and P.

In particular, the expression "non-polar wax" is understood to mean a wax that is constituted solely of non-polar wax, rather than a mixture also comprising other types of waxes that are not non-polar waxes.

As illustrations of non-polar waxes that are suitable for the invention, mention may be made especially of hydrocarbon-based waxes, for instance microcrystalline waxes, paraffin waxes, ozokerite, polyethylene waxes, and their mixture(s).

Polyethylene waxes that may be mentioned include Performalene 500-L Polyethylene and Performalene 400 Polyethylene sold by New Phase Technologies.

An ozokerite that may be mentioned is Ozokerite Wax SP 1020 P.

As microcrystalline waxes that may be used, mention may be made of Multiwax W 445® sold by Sonneborn, and Microwax HW® and Base Wax 30540® sold by Paramelt.

As microwaxes that may be used in the compositions according to the invention as non-polar wax, mention may be made especially of polyethylene microwaxes such as those sold under the names Micropoly 200®, 220®, 220L® and 250S® by Micro Powders.

Preferably, the composition according to the invention comprises a non-polar wax content greater than or equal to 7% by weight relative to the total weight of the composition. The composition according to the invention advantageously comprises a non-polar wax content ranging from 10% to 40% by weight, better from 12% to 30% by weight, relative to the total weight of the composition.

Said composition comprises at least 20% by weight of non-polar wax(es), preferably at least 40% by weight of non-polar wax(es), relative to the total weight of wax(es);

Polar Wax

A composition according to the invention comprises advantageously at least one polar wax.

For the purposes of the present invention, the term "polar wax" means a wax whose solubility parameter $\delta_a$ calculated above its melting point is other than 0 $(J/cm^3)^{1/2}$.

In particular, the term "polar wax" means a wax whose chemical structure is formed essentially from, or even constituted of, carbon and hydrogen atoms, and comprising at least one highly electronegative heteroatom such as an oxygen, nitrogen, silicon or phosphorus atom.

The polar wax(es) may especially be hydrocarbon-based, fluorinated or silicone-based, preferably hydrocarbon-based.

The term "silicone wax" means a wax comprising at least one silicon atom, especially comprising Si—O groups.

The term "hydrocarbon-based wax" means a wax formed essentially from, or even constituted of, carbon and hydrogen atoms, and optionally oxygen and nitrogen atoms, and that does not contain any silicon or fluorine atoms. It may contain alcohol, ester, ether, carboxylic acid, amine and/or amide groups.

As a hydrocarbon-based polar wax, a wax chosen from ester waxes and alcohol waxes is especially preferred.

The expression "ester wax" is understood according to the invention to mean a wax comprising at least one ester function. The expression "alcohol wax" is understood according to the invention to mean a wax comprising at least one alcohol function, i.e. comprising at least one free hydroxyl (OH) group.

In particular, use may be made, preferably, as an ester wax, of those chosen from:

i) Waxes having formula $R_1COOR_2$ in which $R_1$ and $R_2$ denote linear, branched or cyclic aliphatic chains, whose number of atoms varies from 10 to 50, which may contain a heteroatom such as 0, N or P, and whose melting points vary from 25° C. to 120° C. In particular, use may be made, as an ester wax, of a $C_{20}$-$C_{40}$ alkyl(hydroxystearyloxy)stearate (the alkyl group comprising from 20 to 40 carbon atoms), alone or as a mixture, or a $C_{20}$-$C_{40}$ alkyl stearate. Such waxes are especially sold under the names Kester Wax K 82 P®, Hydroxypolyester K 82 P®, Kester Wax K 80 P® and Kester Wax K82H by Koster Keunen. Use may also be made of a glycol and butylene glycol montanate (octacosanoate) such as the wax Licowax KPS Flakes (INCI name: glycol montanate) sold by Clariant.

ii) di(1,1,1-trimethylolpropane)tetrastearate, sold under the name Hest 2T-4S® by Heterene.

iii) diester waxes of a dicarboxylic acid having general formula $R^3$—(—OCO—$R^4$—OCO—$R^5$), in which $R^3$ and $R^5$ are the same or different, preferably the same, and denote a $C_4$-$C_{30}$ alkyl group (alkyl group comprising from 4 to 30 carbon atoms) and $R^4$ denotes a linear or branched $C_4$-$C_{30}$ aliphatic group (alkyl group comprising from 4 to 30 carbon atoms) that may or may not contain one or more unsaturated groups, and that is preferably linear and unsaturated;

iv) Mention may also be made of the waxes obtained by catalytic hydrogenation of animal or plant oils having linear or branched $C_8$-$C_{32}$ fatty chains, for example such as hydrogenated jojoba oil, hydrogenated sunflower oil, hydrogenated castor oil, hydrogenated coconut oil, and also the waxes obtained by hydrogenation of castor oil esterified with cetyl alcohol, such as those sold under the names Phytowax ricin 16L64® and 22L73® by Sophim. Such waxes are described in patent application FR-A-2792190 and the waxes obtained by hydrogenation of olive oil esterified with stearyl alcohol such as that sold under the name Phytowax Olive 18 L 57, or else;

v) Beeswax, synthetic beeswax, polyglycerolated beeswax, beeswax esterified with an oxyethylenated group, carnauba wax, candelilla wax, oxypropylenated lanolin wax, rice bran wax, ouricury wax, esparto grass wax, cork fibre wax, sugar cane wax, Japan wax, sumach wax; montan wax, orange wax, laurel wax and hydrogenated jojoba wax.

vi) and their mixture(s);

According to another embodiment, the polar wax may be an alcohol wax. The expression "alcohol wax" is understood according to the invention to mean a wax comprising at least one alcohol function, i.e. comprising at least one free hydroxyl (OH) group.

Alcohol waxes that may be mentioned include for example the wax Performacol 550-L Alcohol from New Phase Technologies, stearyl alcohol and cetyl alcohol.

According to a second embodiment, the polar wax may be a silicone wax such as silicone beeswax, or an alkyl dimethicone such as the $C_{30}$-$C_{45}$ alkyl dimethicone sold under the reference SF1642 by Momentive Performance Materials.

Preferably, the composition according to the invention comprises a polar wax content greater than or equal to 7% by weight relative to the total weight of the composition, and advantageously of polar hydrocarbon-based wax. The composition according to the invention advantageously comprises a polar wax content ranging from 10% to 40% by weight relative to the total weight of the composition, better from 12% to 30% by weight relative to the total weight of the composition.

Preferably, the composition according to the invention comprises at least one non-polar wax and at least one polar wax.

A composition according to the invention advantageously comprises at least 50% by weight of polar wax(es), relative to the total weight of wax(es).

The total content of non-polar wax(es) and the total content of polar wax(es) are such that the weight ratio of non-polar wax(es) to polar wax(es) is greater than or equal to 1/3.

Oil or Organic Solvent

The compositions according to the invention may comprise at least one oil or organic solvent.

The compositions according to the invention may particularly comprise at least one oil chosen from at least one non-volatile oil, at least one volatile oil, and their mixture.

Non-Volatile Oil

"Oil" is understood to mean a fatty substance that is liquid at room temperature (20° C.) and at atmospheric pressure (760 mmHg).

"Non-volatile oil" means an oil that remains on the skin or the keratin fibre at room temperature (20° C.) and at atmospheric pressure (760 mmHg). More specifically, a non-volatile oil has an evaporation rate strictly less than 0.01 mg/cm$^2$/min.

To measure this evaporation rate, 15 g of oil or of oil mixture to be tested are placed in a crystallizing dish 7 cm in diameter, which is placed on a balance located in a large chamber of about 0.3 m$^3$ that is temperature-regulated, at a temperature of 25° C., and hygrometry-regulated, at a relative humidity of 50%. The liquid is allowed to evaporate freely, without stirring it, while providing ventilation by means of a fan (Papst-Motoren, reference 8550 N, rotating at 2700 rpm) placed in a vertical position above the crystallizing dish containing said oil or said mixture, the blades being directed towards the crystallizing dish, 20 cm away from the bottom of the crystallizing dish. The mass of oil remaining in the crystallizing dish is measured at regular intervals. The evaporation rates are expressed in mg of oil evaporated per unit of area (cm$^2$) and per unit of time (minutes).

Said at least one non-volatile oil may be chosen from hydrocarbon-based oils and silicone oils, and their mixtures, preferably among hydrocarbon-based oils.

The non-volatile hydrocarbon-based oils that are suitable for the present invention may be chosen especially from:
hydrocarbon-based oils of plant origin, such as triglycerides formed from fatty acid esters of glycerol, whose fatty acids may have varied chain lengths from C$_4$ to C$_{28}$, where these chains can be linear or branched, saturated or unsaturated; these oils are especially wheatgerm oil, sunflower oil, grapeseed oil, sesame seed oil, corn oil, apricot oil, castor oil, shea oil, avocado oil, olive oil, soybean oil, sweet almond oil, rapeseed oil, cottonseed oil, hazelnut oil, macadamia oil, jojoba oil, palm oil, alfalfa oil, poppy oil, pumpkin oil, sesame seed oil, marrow oil, rapeseed oil, blackcurrant oil, evening primrose oil, millet oil, barley oil, quinoa oil, rye oil, safflower oil, candlenut oil, passion flower oil and musk rose oil; or alternatively caprylic/capric acid triglycerides such as those sold by Stearineries Dubois or those sold under the names Miglyol 810®, 812® and 818® by Sasol;

synthetic ethers containing from 10 to 40 carbon atoms; linear or branched hydrocarbons of inorganic or synthetic origin, other than the polymers according to the invention, such as petrolatum, polybutenes, polydecenes, squalane, and their mixtures;
synthetic esters such as oils having formula R$_1$COOR$_2$ in which R$_1$ denotes a linear or branched fatty acid residue containing from 1 to 40 carbon atoms and R$_2$ denotes an especially branched hydrocarbon-based chain containing from 1 to 40 carbon atoms, on condition that R$_1$+R$_2$≥10, for instance purcellin oil (cetostearyl octanoate), isopropyl myristate, isopropyl palmitate, C12-C15 alkyl benzoate, hexyl laurate, diisopropyl adipate, isononyl isononanoate, 2-ethylhexyl palmitate, isostearyl isostearate, alkyl or polyalkyl octanoates, decanoates or ricinoleates such as propylene glycol dioctanoate; hydroxylated esters such as isostearyl lactate and diisostearyl malate; and pentaerythritol esters;
fatty alcohols that are liquid at room temperature (20° C.) and atmospheric pressure (760 mmHg), with a branched and/or unsaturated carbon-based chain containing from 12 to 26 carbon atoms, for instance octyldodecanol, isostearyl alcohol, oleyl alcohol, 2-hexyldecanol, 2-butyloctanol and 2-undecylpentadecanol,
higher fatty acids such as oleic acid, linoleic acid or linolenic acid, and their mixtures.

The non-volatile silicone oils that are suitable for the present invention may be chosen especially from:
non-volatile polydimethylsiloxanes (PDMS), polydimethylsiloxanes comprising alkyl or alkoxy groups that are pendent and/or at the end of the silicone chain, which groups each have from 2 to 24 carbon atoms, or phenylated silicones, such as phenyl trimethicones, phenyl dimethicones, phenyl(trimethylsiloxy)diphenylsiloxanes, diphenyl dimethicones, diphenyl(methyldiphenyl)trisiloxanes or (2-phenylethyl)trimethylsiloxysilicates.

A composition according to the invention optionally comprises at least one non-volatile hydrocarbon-based oil of plant origin, such as triglycerides constituted of fatty acid esters and glycerol whose fatty acids may have varied chain lengths from C4 to C28, particularly palm and jojoba oil. A composition according to the invention is preferably free of non-volatile silicone oils.

A composition according to the invention is preferably free of non-volatile oil. However, the total content of non-volatile oil(s) in a composition in accordance with the invention may range from 0.01% to 10% by weight, especially from 0.1% to 8% by weight and preferably from 0.25% to 5% by weight relative to the total weight of the composition.

According to a preferred embodiment, a composition according to the invention comprises from 5% by weight of non-volatile oil(s) relative to the total weight of the composition.

Volatile Oil

The composition according to the invention may comprise at least one volatile oil.

The term "volatile oil" means an oil (or non-aqueous medium) that can evaporate on contact with the skin in less than one hour, at room temperature (20° C.) and atmospheric pressure (760 mm Hg). The volatile oil is a volatile cosmetic oil that is liquid at room temperature (20° C.) and atmospheric pressure (760 mmHg). More specifically, a volatile oil has an evaporation rate of between 0.01 and 200 mg/cm²/min, limits included.

This volatile oil may be hydrocarbon-based.

The volatile hydrocarbon-based oil may be chosen from hydrocarbon-based oils containing from 7 to 16 carbon atoms.

The composition according to the invention may contain one or more volatile branched alkane(s). The expression "one or more volatile branched alkane(s)" means, without preference, "one or more volatile branched alkane oil(s)".

As volatile hydrocarbon-based oils containing from 7 to 16 carbon atoms, mention may be made especially of $C_8$-$C_{16}$ branched alkanes, for instance $C_8$-$C_{16}$ isoalkanes (also known as isoparaffins), isododecane, isodecane, isohexadecane and for example the oils sold under the trade names Isopar and Permethyl, $C_8$-$C_{16}$ branched esters such as isohexyl neopentanoate, and their mixtures. Preferably, the volatile hydrocarbon-based oil containing from 8 to 16 carbon atoms is chosen from isododecane, isodecane and isohexadecane, and their mixtures, and is especially isododecane.

The composition according to the invention may contain one or more volatile linear alkane(s). The term "one or more volatile linear alkane(s)" means, without preference, "one or more volatile linear alkane oil(s)".

A volatile linear alkane that is suitable for the invention is liquid at room temperature (20° C.) and at atmospheric pressure (760 mmHg).

A "volatile linear alkane" that is suitable for the invention means a cosmetic linear alkane, which is capable of evaporating on contact with the skin in less than one hour, at room temperature (20° C.) and atmospheric pressure (760 mmHg, i.e. 101 325 Pa), which is liquid at room temperature (20° C.), especially having an evaporation rate ranging from 0.01 to 15 mg/cm²/min, at room temperature (20° C.) and atmospheric pressure (760 mmHg).

The linear alkanes, preferably of plant origin, comprise from 7 to 15 carbon atoms, especially from 9 to 14 carbon atoms and more particularly from 11 to 13 carbon atoms. As examples of linear alkanes that are suitable for the invention, mention may be made of the alkanes described in patent applications WO 2007/068371 and WO 2008/155059 by Cognis (mixtures of distinct alkanes that differ by at least one carbon). These alkanes are obtained from fatty alcohols, which are themselves obtained from coconut oil or palm oil. As examples of linear alkanes that are suitable for the invention, mention may be made of n-heptane (C7), n-octane (C8), n-nonane (C9), n-decane (C10), n-undecane (C11), n-dodecane (C12), n-tridecane (C13), n-tetradecane (C14) and n-pentadecane (C15), and their mixtures, and especially the mixture of n-undecane (C11) and n-tridecane (C13) described in Example 1 of patent application WO 2008/155059 by Cognis. Mention may also be made of n-dodecane (C12) and n-tetradecane (C14) sold by Sasol under the references, respectively, Parafol 12-97 and Parafol 14-97, and also their mixtures.

The linear alkane may be used alone or as a mixture of at least two distinct alkanes that differ from each other by a carbon number of at least 1, and especially a mixture of at least two linear alkanes comprising from 10 to 14 distinct carbon atoms that differ from each other by a carbon number of at least 2, and especially a mixture of C11/C13 volatile linear alkanes or a mixture of C12/C14 linear alkanes, especially an n-undecane/n-tridecane mixture (such a mixture may be obtained according to Example 1 or Example 2 of WO 2008/155059).

As a variant or additionally, the composition prepared may comprise at least one volatile silicone oil or solvent that is compatible with cosmetic use.

The term "silicone oil" means an oil containing at least one silicon atom, and especially containing Si—O groups. According to one embodiment, said composition comprises less than 10% by weight of volatile silicone oil(s), relative to the total weight of the composition, better still less than 5% by weight, or is even free of volatile silicone oil.

Volatile silicone oils that may be mentioned include cyclic polysiloxanes and linear polysiloxanes, and their mixtures. Volatile linear polysiloxanes that may be mentioned include hexamethyldisiloxane, octamethyltrisiloxane, decamethyltetrasiloxane, tetradecamethylhexasiloxane and hexadecamethylheptasiloxane. Volatile cyclic polysiloxanes that may be mentioned include hexamethylcyclotrisiloxane, octamethylcyclotetrasiloxane, decamethylcyclopentasiloxane and dodecamethylcyclohexasiloxane.

As a variant or additionally, the composition prepared may comprise at least one volatile fluoro oil.

The term "fluoro oil" means an oil containing at least one fluorine atom.

Volatile fluoro oils that may be mentioned include nonafluoromethoxybutane and perfluoromethylcyclopentane, and their mixtures.

A composition according to the invention is preferably free of volatile oils. However, at least one volatile oil may be present in a total content ranging from 0.05% to 20% by weight, preferably ranging from 0.1% to 15% by weight and preferentially ranging from 0.1% to 10% by weight relative to the total weight of the composition. In particular, the volatile oil may be present ranging from 0.5% to 5% by weight relative to the total weight of the composition.

According to a preferred embodiment, a composition according to the invention comprises less than 5% by weight of volatile oil(s) relative to the total weight of the composition.

Pasty Fatty Substance

A composition according to the invention may comprise at least one pasty fatty substance.

For the purposes of the present invention, the term "pasty fatty substance" means a fatty compound with a reversible solid/liquid change of state, and comprising at a temperature of 23° C. a liquid fraction and a solid fraction.

In other words, the starting melting point of the pasty compound can be less than 23° C. The liquid fraction of the pasty compound measured at 23° C. can represent 9% to 97% by weight of the compound. This liquid fraction at 23° C. preferably represents between 15% and 85% and more preferably between 40% and 85% by weight.

Preferably, the pasty fatty substances have an end melting point of less than 60° C.

Preferably, the pasty fatty substances have a hardness of less than or equal to 6 MPa.

Preferably, the pasty fatty substances have, in the solid state, a crystalline organization, which is visible by X-ray diffraction characterizations.

For the purpose of the invention, the melting point corresponds to the temperature of the most endothermic peak observed on thermal analysis (DSC) as described in Standard ISO 11357-3; 1999. The melting point of a pasty substance or of a wax may be measured using a differential scanning calorimeter (DSC), for example the calorimeter sold under the name DSC Q2000 by TA Instruments.

As regards the measurement of the melting point and the determination of the end melting point, the sample preparation and measurement protocols are as follows:

A sample of 5 mg of pasty fatty substance, preheated to 80° C. and withdrawn with magnetic stirring using a spatula that is also heated, is placed in a hermetic aluminium capsule, or a crucible. Two tests are performed to ensure the reproducibility of the results.

The measurements are performed on the abovementioned calorimeter. The oven is flushed with nitrogen. Cooling is performed by an RCS 90 heat exchanger. The sample is then subjected to the following protocol: it is first placed at a temperature of 20° C., and then subjected to a first temperature rise passing from 20° C. to 80° C., at a heating rate of 5° C./minute, then is cooled from 80° C. to −80° C. at a cooling rate of 5° C./minute and finally subjected to a second temperature rise passing from −80° C. to 80° C. at a heating rate of 5° C./minute. During the second temperature rise, the variation in the difference between the power absorbed by the empty crucible and the crucible containing the sample of pasty compound or wax as a function of the temperature is measured. The melting point of the compound is the value of the temperature corresponding to the tip of the peak of the curve representing the variation in the difference in power absorbed as a function of the temperature.

The end melting point corresponds to the temperature at which 95% of the sample has melted.

The liquid fraction by weight of the pasty compound at 23° C. is equal to the ratio of the enthalpy of fusion consumed at 23° C. to the enthalpy of fusion of the pasty compound.

The enthalpy of fusion of the pasty compound is the enthalpy consumed by the compound in order to pass from the solid state to the liquid state. The pasty compound is said to be in the solid state when all of its mass is in crystalline solid form. The pasty compound is said to be in the liquid state when all of its mass is in liquid form.

The enthalpy of fusion of the pasty compound is equal to the integral of the entire melting curve obtained using the abovementioned calorimeter, with a temperature rise of 5 or 10° C. per minute, according to standard ISO 11357-3:1999. The enthalpy of fusion of the pasty compound is the amount of energy required to make the compound change from the solid state to the liquid state. It is expressed in J/g.

The enthalpy of fusion consumed at 23° C. is the amount of energy absorbed by the sample to change from the solid state to the state that it has at 23° C., composed of a liquid fraction and a solid fraction.

The liquid fraction of the pasty compound measured at 32° C. preferably represents from 30% to 100% by weight of the compound, preferably from 50% to 100%, more preferably from 60% to 100% by weight of the compound. When the liquid fraction of the pasty compound measured at 32° C. is equal to 100%, the temperature of the end of the melting range of the pasty compound is less than or equal to 32° C.

The liquid fraction of the pasty compound measured at 32° C. is equal to the ratio of the enthalpy of fusion consumed at 32° C. to the enthalpy of fusion of the pasty compound. The enthalpy of fusion consumed at 32° C. is calculated in the same way as the enthalpy of fusion consumed at 23° C.

As regards the measurement of the hardness, the sample preparation and measurement protocols are as follows:

The pasty fatty substance is placed in a mould 75 mm in diameter, which is filled to about 75% of its height. In order to overcome the thermal history and to control the crystallization, the mould is placed in a Vötsch VC 0018 programmable oven, where it is first placed at a temperature of 80° C. for 60 minutes, then cooled from 80° C. to 0° C. at a cooling rate of 5° C./minute, and then left at the stabilized temperature of 0° C. for 60 minutes, and then subjected to a temperature rise passing from 0° C. to 20° C. at a heating rate of 5° C./minute, and then left at the stabilized temperature of 20° C. for 180 minutes.

The compression force measurement is performed using a TA/TX2i texturometer from Swantech. The spindle used is chosen according to the texture:
cylindrical steel spindle 2 mm in diameter for very rigid starting materials;
cylindrical steel spindle 12 mm in diameter for sparingly rigid starting materials.

The measurement comprises three steps: a first step after automatic detection of the surface of the sample, where the spindle moves at a measuring speed of 0.1 mm/s, and penetrates into the pasty fatty substance to a penetration depth of 0.3 mm, the software notes the maximum force value reached; a second "relaxation" step where the spindle remains at this position for one second and the force is noted after 1 second of relaxation; finally, a third "withdrawal step" in which the spindle returns to its initial position at a speed of 1 mm/s, and the probe withdrawal energy (negative force) is noted.

The hardness value measured during the first step corresponds to the maximum compression force measured in Newtons divided by the area of the texturometer cylinder expressed in $mm^2$ in contact with the pasty fatty substance. The hardness value obtained is expressed in megapascals or MPa.

The pasty fatty substance is preferably chosen from synthetic compounds and compounds of plant origin. A pasty compound may be obtained by synthesis from starting materials of plant origin.

The pasty compound is advantageously chosen from:
lanolin and its derivatives,
petrolatum, especially the product having this as INCI name and that is sold under the name Ultima White PET USP by Perenco,
polyol ethers chosen from polyalkylene glycol pentaerythrityl ethers, fatty alcohol ethers of sugars, and their mixtures, polyethylene glycol pentaerythrityl ether comprising five ethylene oxide (5 EO) units (CTFA name: PEG-5 Pentaerythrityl Ether), the polypropylene glycol pentaerythrityl ether comprising 5 propylene oxide (5 PO) units (CTFA name: PPG-5 Pentaerythrityl Ether) and their mixtures, and more especially the mixture PEG-5 Pentaerythrityl Ether, PPG-5 Pentaerythrityl Ether and soybean oil, sold under the name Lanolide by Vevy, which is a mixture in which the constituents are in a 46/46/8 weight ratio: 46% PEG-5 Pentaerythrityl Ether, 46% PPG-5 Pentaerythrityl Ether and 8% soybean oil;
polymeric or non-polymeric silicone compounds
polymeric or non-polymeric fluoro compounds
vinyl polymers, especially:
olefin homopolymers and copolymers,
hydrogenated diene homopolymers and copolymers,
linear or branched oligomers that are homopolymers or copolymers of alkyl(meth)acrylates preferably containing a $C_8$-$C_{30}$ alkyl group,
oligomers that are homopolymers and copolymers of vinyl esters containing $C_8$-$C_{30}$ alkyl groups,
oligomers that are homopolymers and copolymers of vinyl ethers containing $C_8$-$C_{30}$ alkyl groups, liposoluble polyethers resulting from the polyetherification between one or more $C_2$-$C_{100}$ and preferably $C_2$-$C_{50}$ diols, esters, and/or their mixtures.

The pasty compound is preferably a polymer, especially a hydrocarbon-based polymer.

Among the liposoluble polyethers that are particularly preferred are copolymers of ethylene oxide and/or of propylene oxide with $C_6$-$C_{30}$ long-chain alkylene oxides, more preferably such that the weight ratio of the ethylene oxide and/or of the propylene oxide to alkylene oxides in the copolymer is from 5:95 to 70:30. In this family, mention will be made especially of copolymers such that the long-chain alkylene oxides are arranged in blocks having an average molecular weight from 1000 to 10 000, for example a polyoxyethylene/polydodecyl glycol block copolymer such as the ethers of dodecanediol (22 mol) and of polyethylene glycol (45 EO) sold under the brand name Elfacos ST9 by Akzo Nobel.

Among the esters, the following are especially preferred:
esters of a glycerol oligomer, especially diglycerol esters, especially condensates of adipic acid and of glycerol, for which some of the hydroxyl groups of the glycerols have reacted with a mixture of fatty acids such as stearic acid, capric acid, stearic acid and isostearic acid, and 12-hydroxystearic acid, preferably such as bis-diglyceryl polyacyladipate-2 sold under the brand name Softisan 649 by Sasol, the arachidyl propionate sold under the brand name Waxenol 801 by Alzo, phytosterol esters, fatty acid triglycerides and their derivatives, for instance triglycerides of fatty acids, which are especially $C_{10}$-$C_{18}$, and partially or totally hydrogenated such as those sold under the reference Softisan 100 by Sasol, pentaerythritol esters, and their mixtures.

esters of a diol dimer and of a diacid dimer, where appropriate esterified on their free alcohol or acid functional group(s) with acid or alcohol radicals, especially dimer dilinoleate esters; such esters may be chosen especially from the esters having the following INCI nomenclature: Bis-Behenyl/Isostearyl/Phytosteryl Dimer Dilinoleyl Dimer Dilinoleate (Plandool G), Phytosteryl/Isostearyl/Cetyl/Stearyl/Behenyl Dimer Dilinoleate (Plandool H or Plandool S), and their mixtures, mango butter, such as the product sold under the reference Lipex 203 by AarhusKarlshamn, shea butter, especially the product for which the INCI name is Butyrospermum Parkii Butter, such as the product sold under the reference Sheasoft® by AarhusKarlshamn, and their mixtures.

Among the pasty compounds, bis-behenyl/iso-stearyl/phytosteryl dimer dilinoleyl, bis(diglyceryl)poly(2-acyladipate), hydrogenated castor oil dimer dilinoleate, for example Risocast DA-L sold by Kokyu Alcohol Kogyo, and hydrogenated castor oil isostearate, for example Salacos HCIS (V-L) sold by Nisshin Oil, mango butter, shea butter, vinylpyrrolidone/eicosene copolymers, or their mixture(s), will preferably be chosen.

A composition according to the invention is preferably free of pasty fatty substances. However, a composition according to the invention may comprise one or more pasty fatty substances at a total content greater than or equal to 0.01% by weight relative to the total weight of the composition, for example between 0.1% and 5% by weight relative to the total weight of the composition.

Emulsifying System According to the Invention

A composition according to the invention comprises as main emulsifying system at least two anionic surfactants.

The term "main emulsifying system" means a system which, in its absence, does not lead to the formation of a stable composition.

The term "stable" means a composition which, after having been placed in an oven at 45° C. for two months, does not have, after returning to room temperature, any grains that are perceptible to the touch, when a thin layer of the composition is sheared between the fingers.

More specifically, an emulsifying system in accordance with the present invention comprises:
at least one $C_{12}$-$C_{22}$ monoalkyl phosphate,
at least one acylglutamate such as Disodium hydrogenated tallow glutamate (Amisoft HS-21 R® sold by Ajinomoto),
and their mixture(s).

$C_{12}$-$C_{22}$ Monoalkyl phosphates

A composition according to the invention comprises at least one $C_{12}$-$C_{22}$ monoalkyl phosphate.

The term monoalkyl is understood to mean that the phosphate element is combined with a single $C_{12}$-$C_{22}$ alkyl chain, unless otherwise specified. The monoalkyl phosphate(s) (including phosphine oxide(s)) that may be used in compositions according to the present application is/are chosen from $C_{12}$-$C_{22}$, preferably $C_{16}$-$C_{18}$, monoalkyl phosphates, and their mixtures.

In a preferred manner, they are chosen from monocetyl phosphate, monostearyl phosphate and monocetearyl phosphate.

More specifically, it is monocetyl phosphate, for example sold under the names Amphisol K (Roche), Amphisol A (Roche), Arlatone MAP (Uniqema), crodafos MCA (Croda).

the total $C_{12}$-$C_{22}$ monoalkyl phosphate content is preferably greater than or equal to 0.5% by weight, relative to the total weight of the composition;

The total $C_{12}$-$C_{22}$ monoalkyl phosphate content ranges advantageously from 1 to 20% by weight, preferably from 2 to 12% by weight relative to the total weight of the composition, better from 3 to 10% by weight relative to the total weight of the composition.

Acyl Glutamic Acid(s) and their Salt(s)

Acyl glutamic acid(s) is understood in the description to be acyl glutamic acid(s) and their salt(s).

A composition according to the invention comprises at least one acyl glutamic acid having at least one $C_{12}$-$C_{22}$ acyl chain, their salt(s) (glutamates), and their mixture(s).

In particular, acyl glutamic acid(s) (INCI name: acyl glutamic acid), their salts (glutamates), and their mixtures, is (are) chosen from acyl glutamic acids having a $C_{12}$-$C_{22}$ acyl chain, and the salts of alkali metals such as Na, Li, K, preferably Na or K, salts of alkaline earth metals such as Mg and ammonium salts of said acids, and their mixture(s).

More preferably, acyl glutamic acid(s) (INCI name: acyl glutamic acid), their salts (glutamates), and their mixtures, is (are) preferably chosen from lauroyl glutamic acid, myristoyl glutamic acid, palmitoyl glutamic acid, stearoyl glutamic acid, behenoyl glutamic acid, olivoyl glutamic acid, cocoyl glutamic acid and the alkali metals salts such as Na, Li, K, preferably Na or K, alkaline earth metal salts such as Mg and ammonium salts of said acids, and their mixture(s).

Mention may be made especially of compounds with the INCI names lauroyl glutamic acid, cocoyl glutamic acid, sodium stearoyl glutamate, potassium lauroyl glutamate, potassium cocoyl glutamate, sodium olivoyl glutamate, and their mixture(s).

Such compounds are sold under the name AMISOFT by AJINOMOTO and especially under the references Amisoft CA, Amisoft LA, Amisoft HS 11 PF, Amisoft MK-11, Amisoft LK-11, Amisoft CK-11, or else sold by Keminova Italiana SRL.

As acyl glutamic acid salt(s), mention may also be made of disodium hydrogenated tallow glutamate such as that sold under the reference Amisoft HS-21 by Ajinomoto.

Mention may also be made of commercially available surfactant mixtures comprising at least one acyl glutamic acid salt, for example the mixture of acyl glutamate salts, such as Amisoft LS-22 sold by Ajinomoto.

According to a specific embodiment, the monosodium salt of n-stearoyl-L-glutamic acid is used, more specifically that sold by Ajinomoto under the reference Amisoft HS-11.

The total acyl glutamic acid content is preferably greater than or equal to 0.5% by weight relative to the total weight of the composition.

The total acyl glutamic acid content ranges advantageously from 1 to 20% by weight, preferably from 2 to 12% by weight relative to the total weight of the composition, better from 3 to 10% by weight relative to the total weight of the composition.

The total $C_{12}$-$C_{22}$ monoalkyl phosphate content and the total acyl glutamic acid content are such that the weight ratio of $C_{12}$-$C_{22}$ monoalkyl phosphate(s) to acyl glutamic acid(s) is inclusively comprised between 1/3 and 3, preferably between 3/5 and 5/3.

The total $C_{12}$-$C_{22}$ monoalkyl phosphate content plus the total acyl glutamic acid content and the total wax content are such that the weight ratio of $C_{12}$-$C_{22}$ monoalkyl phosphate(s) together with the acyl glutamic acid(s), relative to the wax(es), is greater than or equal to 1/10, preferably comprised between 1/8 and 1/2, more preferably between 1/4 and 1/3. Such a ratio is thus obtained using the following calculation: (total $C_{12}$-$C_{22}$ monoalkyl phosphate content+ total acyl glutamic acid content)/total wax content.

Additional Surfactant(s)

A composition according to the invention may comprise one or more additional surfactant(s), distinct from the $C_{12}$-$C_{20}$ monoalkyl phosphate(s) and the acyl glutamic acid(s).

Preferably, a composition according to the invention comprises at least one additional surfactant.

A composition according to the invention may comprise one or more additional surfactant(s) chosen from at least one non-ionic surfactant.

This non-ionic surfactant is especially chosen from:
at least one non-ionic surfactant having at 25° C. an HLB balance (hydrophilic-lipophilic balance) within the Griffin sense of less than 8,
at least one non-ionic emulsifying surfactant having at 25° C. an HLB balance (hydrophilic-lipophilic balance) within the Griffin sense of more than 8,
and their mixture(s).

"Less than" is understood to be strictly less than or equal to, or preferably strictly less than.

"Greater than" is understood to be strictly greater than or equal to, or preferably strictly greater than.

The Griffin HLB value is defined in J. Soc. Cosm. Chem., 1954 (volume 5), pages 249-256.

Reference may be made to Kirk-Othmer's *Encyclopedia of Chemical Technology*, Volume 22, pp. 333-432, 3rd Edition, 1979, Wiley, for the definition of the emulsifying properties and functions of surfactants, especially pp. 347-377 of this reference, for the non-ionic surfactants.

Non-Ionic Surfactant(s) with HLB Less than 8 at 25° C.

The non-ionic surfactant(s) with HLB less than 8 at 25° C. is (are) preferably chosen from:
monosaccharide esters and ethers such as sucrose stearate, sucrose cocoate, sorbitan stearate, sorbitan monoisostearate, sorbitan tristearate, sorbitan oleate, sorbitan sesquioleate, methylglucose isostearate, sucrose (poly) palmitostearate, sucrose laurate, sucrose palmitate, sucrose tribehenate, sucrose oleate, sucrose distearate, sucrose polylaurate, sucrose hexaerucate, and their mixtures, for example Arlatone 2121® sold by ICI or Span 65V from Uniqema;
esters of fatty acids, especially of $C_8$-$C_{24}$ and preferably of $C_{16}$-$C_{22}$ fatty acids, and of polyol, especially of glycerol or sorbitol, such as glyceryl stearate, sold, for example, under the name Tegin M® by Goldschmidt, polyglyceryl diisostearate, polyglyceryl isostearate, polyglyceryl monostearate, diglyceryl tetraisostearate, polyethylene glycol diisostearate, polyglyceryl-10 pentastearate, glyceryl monooleate, glyceryl laurate, such as the product sold under the name Imwitor 312® by Hüls, diethylene glycol (di)laurate, decaglyceryl pentaoleate, decaglyceryl pentadiisostearate, glyceryl caprate/caprylate, polyglyceryl-2(iso)stearate and glyceryl(poly)ricinoleate;
oxyalkylenated alcohols, especially oxyethylenated and/or oxypropylenated alcohols, which may comprise from 1 to 5 ethylene oxide and/or propylene oxide units, especially ethoxylated $C_8$-$C_{24}$ and preferably $C_{12}$-$C_{18}$ fatty alcohols such as stearyl alcohol ethoxylated with 2 ethylene oxide units (CTFA name: Steareth-2) such as Brij 72 sold by Uniqema, or oxyethylenated oleyl alcohol;
oxyethylenated and/or oxypropylenated silicone compounds, for example containing from 3 to 20 oxyalkylene units and especially oxyethylenated and/or oxypropylenated dimethicones; it should be noted that when a polyoxyalkylenated or polyglycerolated organopolysiloxane elastomer, referred to as being emulsifying, where appropriate conveyed in a non-volatile oil, as described above, is used, it may simultaneously be the surfactant and the organopolysiloxane elastomer of the composition in accordance with the invention;
the mixture of cyclomethicone/dimethicone copolyol sold under the name Q2-3225C® by Dow Corning; and their mixture(s).

Non-Ionic Surfactant(s) with HLB Greater than 8 at 25° C.

The non-ionic surfactant(s) with HLB greater than 8 at 25° C. is (are) preferably chosen from:
oxyalkylenated glycerol ethers, particularly oxyethylenated ethers, that may contain from 5 to 100 ethylene oxide units;
oxyalkylenated alcohols, especially oxyethylenated alcohols, that may comprise from 5 to 100 ethylene oxide units, preferably from 10 to 50 ethylene oxide units, especially fatty alcohols, especially ethoxylated $C_8$-$C_{24}$ fatty alcohols, and preferably ethoxylated $C_{12}$-$C_{18}$ fatty alcohols, such as stearyl alcohol ethoxylated with 20 ethylene oxide units (CTFA name Steareth-20) such as Brij 78 sold by Uniqema, cetyl alcohol ethoxylated with 20 ethylene oxide units (CTFA name Ceteth-20), cetearyl alcohol ethoxylated with 30 ethylene oxide units (CTFA name Ceteareth-30) and the mixture of $C_{12}$-$C_{15}$ fatty alcohols comprising 7 ethylene oxide units (CTFA name $C_{12-15}$ Pareth-7) such as that sold under the name Neodol 25-7® by Shell Chemicals;

fatty acid esters, especially $C_8$-$C_{24}$ fatty acid esters, and preferably $C_{16}$-$C_{22}$ fatty acid esters, of polyethylene glycol (or PEG) (that may comprise from 5 to 100 ethylene oxide units), such as PEG-50 stearate and PEG-40 monostearate sold under the name Myrj 52P® by Uniqema, or else PEG-75 stearate;

fatty acid esters, especially $C_8$-$C_{24}$ and preferably $C_{16}$-$C_{22}$ fatty acid esters, of oxyalkylenated, particularly oxyethylenated, glycerol ethers (which may comprise from 5 to 200 ethylene oxide units), for instance glyceryl monostearate polyoxyethylenated with 200 ethylene oxide units, sold under the name Simulsol 220 TM® by Seppic; glyceryl stearate polyoxyethylenated with 30 ethylene oxide units, for instance the product Tagat S® sold by Goldschmidt, glyceryl oleate polyoxyethylenated with 30 ethylene oxide units, for instance the product Tagat O® sold by Goldschmidt, glyceryl cocoate polyoxyethylenated with 30 ethylene oxide units, for instance the product Varionic LI 13® sold by Sherex, glyceryl isostearate polyoxyethylenated with 30 ethylene oxide units, for instance the product Tagat L® sold by Goldschmidt, and glyceryl laurate polyoxyethylenated with 30 ethylene oxide units, for instance the product Tagat I® from Goldschmidt;

fatty acid esters, especially $C_8$-$C_{24}$ fatty acid esters and preferably $C16$-$C_{22}$ fatty acid esters, of oxyalkylenated sorbitol ethers, particularly oxyethylenated (which may comprise from 5 to 100 ethylene oxide units), for instance polysorbate 60 sold under the name Tween 60® by Uniqema;

dimethicone copolyol, such as the product sold under the name Q2-5220® by Dow Corning;

dimethicone copolyol benzoate, such as the product sold under the names Finsolv SLB 101® and 201® by Fintex;

copolymers of propylene oxide and of ethylene oxide, also known as EO/PO polycondensates;

and their mixtures.

EO/PO polycondensates are more particularly copolymers formed from polyethylene glycol and polypropylene glycol blocks, for instance polyethylene glycol/polypropylene glycol/polyethylene glycol triblock polycondensates. These triblock polycondensates have, for example, the following chemical structure:

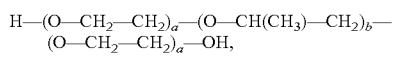

in which formula a ranges from 2 to 120 and b ranges from 1 to 100.

The EO/PO polycondensates preferably have a weight-average molecular weight ranging from 1000 to 15 000 and better still ranging from 2000 to 13 000. Advantageously, said EO/PO polycondensates have a cloud point, at 10 g/l in distilled water, of greater than or equal to 20° C., preferably of greater than or equal to 60° C. The cloud point is measured according to the standard ISO 1065. Mention may be made, as EO/PO polycondensate that can be used according to the invention, of the polyethylene glycol/polypropylene glycol/polyethylene glycol triblock polycondensates sold under the Synperonic® names, such as Synperonic PE/L44® and Synperonic PE/F127®, by ICI.

According to an advantageous embodiment, a composition according to the invention comprises at least one non-ionic surfactant with HLB less than 8 at 25° C.

According to an advantageous embodiment, the non-ionic surfactant(s) with HLB less than 8 are chosen from a monosaccharide ester or ether, a glycerol fatty acid ester, an oxyalkylenated alcohol with 1 to 5 alkoxyl unit(s), and their mixture(s). In a specific embodiment, a composition according to the invention comprises an oxyalkylenated alcohol with 1 to 5 ethylene oxide unit(s), particularly 2 ethylene oxide units (also called Steareth 2).

The additional surfactant(s) may be present in a total content ranging from 0.1% to 10% by weight, advantageously from 0.5% to 5% by weight relative to the total weight of the composition.

According to one specific embodiment, the cosmetic composition according to the present invention comprises less than 1%, preferably less than 0.5% by weight of triethanolamine, and better still is free of triethanolamine.

According to one specific embodiment, the cosmetic composition according to the present invention comprises less than 1%, preferably less than 0.5% by weight of triethanolamine stearate, and better still is free of triethanolamine stearate.

Preferably, a composition according to the invention comprises less than 2% by weight of additional emulsifying system relative to the total weight of the composition, even less than 1% by weight, and most preferably is free of additional surfactant. Specifically, a composition according to the invention is preferably free of additional ionic surfactant, particularly of additional anionic surfactant, and of additional non-ionic surfactant.

Co-Surfactant(s)

According to one particular embodiment, the compositions according to the invention comprise at least one co-surfactant. This (these) co-surfactant(s) is (are) advantageously chosen from fatty alcohols. The fatty alcohol(s) comprise(s) from 10 to 30 carbon atoms, preferably from 10 to 26 carbon atoms, better still from 10 to 24 carbon atoms and even better still from 14 to 22 carbon atoms.

This (these) co-surfactants may be present in the composition in a total content of between 0.1% and 5% by weight and better still between 1% and 4% by weight relative to the total weight of the composition.

Film-Forming Polymer

The compositions according to the present patent application preferably comprise at least one hydrophilic or lipophilic film-forming polymer, preferably a hydrophilic film-forming polymer.

In the present patent application, "film-forming polymer" means a polymer that can, by itself or in the presence of an auxiliary film-forming agent, form a macroscopically continuous film, and preferably a cohesive deposit, and better still a deposit whose cohesion and mechanical properties are such that said deposit can be isolated and manipulated individually, for example when said deposit is prepared by pouring onto a non-stick surface such as a Teflon-coated or silicone-coated surface.

In general, the solids content of the "film-forming polymer" in compositions according to the present patent application ranges from 0.1% to 40%, preferably from 0.5% to 30% and better still from 1% to 10% by weight relative to the total weight of the composition.

The hydrophilic film-forming polymer may be a water-soluble polymer or may be in dispersion in an aqueous medium.

Among the film-forming polymers that can be used in the composition of the present invention, mention may be made of synthetic polymers, of free-radical type or of polycondensate type, and polymers of natural origin, and their mixtures.

Examples of water-soluble film-forming polymers that may be mentioned include:
- proteins, for instance proteins of plant origin such as wheat or soybean proteins; proteins of animal origin such as keratins, for example keratin hydrolysates and sulfonic keratins;
- cellulose polymers such as hydroxyethylcellulose, hydroxypropylcellulose, methylcellulose, ethylhydroxyethylcellulose and carboxymethylcellulose, and also quaternized cellulose derivatives;
- acrylic polymers or copolymers, such as polyacrylates or polymethacrylates;
- vinyl polymers, for instance polyvinylpyrrolidones, copolymers of methyl vinyl ether and of malic anhydride, the copolymer of vinyl acetate and of crotonic acid, copolymers of vinylpyrrolidone and of vinyl acetate; copolymers of vinylpyrrolidone and of caprolactam; polyvinyl alcohol;
- anionic, cationic, amphoteric or non-ionic chitin or chitosan polymers;
- gums arabic, guar gum, xanthan derivatives, karaya gum, acacia gum;
- alginates and carrageenans;
- glycoaminoglycans, hyaluronic acid and its derivatives;
- shellac resin, sandarac gum, dammars, elemis and copals;
- deoxyribonucleic acid;
- mucopolysaccharides such as chondroitin sulfates;
- and their mixtures.

The film-forming polymer may also be present in the composition in the form of particles dispersed in an aqueous phase, which is generally known as a latex or pseudolatex. The techniques for preparing these dispersions are well known to those skilled in the art.

Aqueous dispersions of film-forming polymer that may be used include the acrylic dispersions sold under the names Neocryl XK-90®, Neocryl A-1070®, Neocryl A-1090®, Neocryl BT-62®, Neocryl A-1079® and Neocryl A-523® by Avecia-Neoresins, Dow Latex 432® by Dow Chemical, Daitosol 5000 AD® or Daitosol 5000 SJ® by Daito Kasey Kogyo; Syntran 5760® by Interpolymer, Allianz Opt® by Rohm & Haas or the aqueous polyurethane dispersions sold under the names Neorez R-981® and Neorez R-974® by Avecia-Neoresins, Avalure UR-405®, Avalure UR-410®, Avalure UR-425,® Avalure UR-450®, Sancure 875®, Avalure UR-445® and Sancure 2060® by Noveon, Impranil 85® by Bayer, Aquamere H-1511® by Hydromer; the sulfopolyesters sold under the brand name Eastman AQ® by Eastman Chemical Products, vinyl dispersions, for instance Mexomer PAM®, aqueous polyvinyl acetate dispersions, for instance Vinybran® from Nisshin Chemical or those sold by Union Carbide, aqueous dispersions of vinylpyrrolidone, dimethylaminopropylmethacrylamide and lauryldimethylpropylmethacrylamidoammonium chloride terpolymer, such as Styleze W from ISP, aqueous dispersions of polyurethane/polyacrylic hybrid polymers such as those sold under the references Hybridur® by Air Products or Duromer® from National Starch, core/shell type dispersions: for example those sold by Atofina under the reference Kynar (core: fluoro, shell: acrylic) or those described in document U.S. Pat. No. 5,188,899 (core: silica, shell: silicone), and their mixtures.

A composition according to the invention may also comprise as a variant of or additionally a lipophilic polymer that may be in solution or in dispersion in a non-aqueous solvent phase.

Dyestuffs

The compositions in accordance with the invention comprise at least one dyestuff.

This (or these) dyestuff(s) is (are) preferably chosen from pulverulent dyestuffs, liposoluble dyes and water-soluble dyes, and their mixtures.

Preferably, the compositions according to the invention comprise at least one pulverulent dyestuff. The pulverulent dyestuffs may be chosen from pigments and nacres, preferably from pigments.

The pigments may be white or coloured, inorganic and/or organic, and coated or uncoated. Among the inorganic pigments, mention may be made of metal oxides, especially titanium dioxide, optionally surface-treated, zirconium, zinc or cerium oxide, and also iron, titanium or chromium oxide, manganese violet, ultramarine blue, chromium hydrate and ferric blue. Among the organic pigments that may be mentioned are carbon black, pigments of D & C type and lakes based on cochineal carmine or on barium, strontium, calcium or aluminium.

The nacres may be chosen from white nacreous pigments such as mica coated with titanium or with bismuth oxychloride, coloured nacreous pigments such as titanium mica with iron oxides, titanium mica especially with ferric blue or chromium oxide, titanium mica with an organic pigment of the abovementioned type, and also nacreous pigments based on bismuth oxychloride.

The liposoluble dyes are, for example, Sudan Red, D&C Red 17, D&C Green 6, β-carotene, soybean oil, Sudan Brown, D&C Yellow 11, D&C Violet 2, D&C Orange 5, quinoline yellow and annatto.

Preferably, the pigments contained in the compositions according to the invention are chosen from metal oxides.

These dyestuffs may be present in a content ranging from 0.01% to 30% by weight, relative to the total weight of the composition, especially from 3% to 15% by weight, relative to the total weight of the composition.

Preferably, the dyestuff(s) is (are) chosen from one or more metal oxide(s) present in a content of greater than or equal to 2% by weight relative to the total weight of the composition, advantageously inclusively between 3% and 15% by weight relative to the total weight of the composition.

Fillers

The compositions in accordance with the invention may also comprise at least one filler.

The fillers may be selected from those that are well known to those skilled in the art and commonly used in cosmetic compositions. The fillers may be inorganic or organic, and lamellar or spherical. Mention may be made of talc, mica, silica, kaolin, polyamide powders, for instance the Nylon® sold under the name Orgasol® by Atochem, poly-β-alanine powders and polyethylene powders, powders of tetra-fluoroethylene polymers, for instance Teflon®, lauroyllysine, starch, boron nitride, expanded polymeric hollow microspheres such as those of polyvinylidene chloride/acrylonitrile, for instance those sold under the name Expancel® by Nobel Industrie, acrylic powders such as those sold under the name Polytrap® by Dow Corning, polymethyl methacrylate particles and silicone resin microbeads (for example Tospearls® from Toshiba), precipitated calcium carbonate, magnesium carbonate and basic magnesium carbonate, hydroxyapatite, hollow silica microspheres (Silica Beads® from Maprecos), glass or ceramic microcapsules, metal soaps derived from organic carboxylic acids having from 8 to 22 carbon atoms and especially from 12 to 18 carbon atoms, for example zinc, magnesium or lithium stearate, zinc laurate and magnesium myristate.

It is also possible to use a compound that is capable of swelling on heating, and especially heat-expandable particles such as non-expanded microspheres of vinylidene chloride/acrylonitrile/methyl methacrylate copolymer or of acrylonitrile homopolymer copolymer, for instance those sold, respectively, under the references Expancel® 820 DU 40 and Expancel® 007WU by Akzo Nobel.

The fillers may represent from 0.1% to 25% by weight and especially from 0.2% to 20% by weight relative to the total weight of the composition.

Fibres

The compositions in accordance with the invention may also comprise at least one fibre that can improve the lengthening effect.

In the case of making a top coat containing fibres intended to coat a base-coat composition according to the invention, the inventors have been able to observe that the non-volatile oil according to the invention made positioning the fibres at the end of natural eyelashes easier.

"Fibre" should be understood as meaning an object of length L and of diameter D such that L is very much greater than D, D being the diameter of the circle in which the cross section of the fibre is inscribed. In particular, the ratio L/D (or aspect ratio) is chosen in the range from 3.5 to 2500, especially from 5 to 500 and more particularly from 5 to 150.

The fibres that may be used in the composition of the invention may be inorganic or organic fibres, of synthetic or natural origin. They may be short or long, individual or organized, for example braided, and hollow or solid. They may have any shape and may especially have a circular or polygonal (square, hexagonal or octagonal) cross section depending on the specific application envisaged. In particular, their ends are blunted and/or polished to prevent injury.

In particular, the fibres have a length ranging from 1 μm to 10 mm, especially from 0.1 mm to 5 mm and more particularly from 0.3 mm to 3.5 mm. Their cross section may be included in a circle with a diameter ranging from 2 nm to 500 μm, especially ranging from 100 nm to 100 μm and more particularly from 1 μm to 50 μm. The weight or yarn count of fibres is often given in denier or decitex and represents the weight in grams per 9 km of yarn. The fibres according to the invention can especially have a count chosen within the range from 0.15 to 30 denier and especially from 0.18 to 18 denier.

The fibres that may be used in the composition of the invention may be chosen from rigid or non-rigid fibres, and may be inorganic or organic fibres, of synthetic or natural origin.

Moreover, the fibres may or may not be surface-treated, may be coated or uncoated, and may be coloured or uncoloured.

As fibres that may be used in the composition according to the invention, mention may be made of non-rigid fibres such as polyamide (Nylon®) fibres or rigid fibres such as polyimideamide fibres, for instance those sold under the names Kermel® and Kermel Tech® by Rhodia or poly(p-phenyleneterephthalamide) (or aramid) fibres sold especially under the name Kevlar® by DuPont de Nemours.

The fibres may be present in the composition according to the invention in a content ranging from 0.01% to 10% by weight, especially from 0.1% to 5% by weight and more particularly from 0.3% to 3% by weight relative to the total weight of the composition.

Cosmetic Active Agents

The compositions in accordance with the invention may also comprise at least one cosmetic active agent.

As cosmetic active agents that may be used in the compositions in accordance with the invention, mention may be made especially of antioxidants, preserving agents, fragrances, neutralizers, emollients, thickeners, coalescers, plasticizers, moisturizers, vitamins and screening agents, especially sunscreens, and their mixtures.

Needless to say, a person skilled in the art will take care to select the optional additional additives and/or their amount such that the advantageous properties of the composition according to the invention are not, or are not substantially, adversely affected by the envisaged addition.

Preferably, the composition according to the invention is a leave-in composition. Advantageously, the composition is a make-up composition and especially a mascara.

Assembly

An assembly for coating keratin fibres according to the invention may comprise an applicator suitable for applying said cosmetic composition for coating keratin fibres and, where appropriate, a packaging device suitable for receiving said composition.

Applicator

The applicator may comprise means for smoothing and/or separating keratin fibres, such as the eyelashes or the eyebrows, especially in the form of teeth, bristles or other reliefs.

The applicator is arranged to apply the composition to the eyelashes or the eyebrows, and may comprise, for example, a brush or a comb.

The applicator may also be used for finishing of the make-up, over a region of the eyelashes or eyebrows that is made up or laden with composition.

The brush may comprise a twisted core and bristles held between the turns of the core, or may be made in yet another way.

The comb is, for example, produced from a single part by moulding of a plastic.

In certain embodiments, the application member is mounted at the end of a wand, which wand may be flexible, which may contribute to improving comfort during application.

Packaging Device

The packaging device may comprise a container for housing the composition for coating keratin fibres. This composition may then be withdrawn from the container by immersing the applicator therein.

This applicator may be firmly attached to a member for closing the container. This closing member may form a member for gripping the applicator. This gripping member may form a cap to be removably mounted on said container by any suitable means, such as screwing, click-fastening, shrink fitting, etc. Such a container may thus reversibly house said applicator.

This container can be optionally equipped with a wiper suitable for removing a surplus of product taken by the applicator.

A method for applying the composition according to the invention to the eyelashes or the eyebrows may also include the following steps:

forming a deposit of the cosmetic composition on the eyelashes or the eyebrows, leaving the deposit on the eyelashes or the eyebrows, it being possible for the deposit to dry.

It should be noted that, according to another embodiment, the applicator may form a product container. In such a case, a container may, for example, be provided for in the gripping member and an internal channel can internally connect this gripping member to the application members in relief.

Finally, it should be noted that the packaging and application assembly may be in the form of a kit, it being possible for the applicator and the packaging device to be housed separately in one and the same packaging article.

The preceding examples and those that follow are given as illustrations of the present invention, and shall not limit its scope.

EXAMPLES

1/ Preparation of a Mascara Composition According to the Invention Compared with Two Mascara Composition Outside the Invention

| Phase | Ingredients with contents as a percentage | Composition according to the invention | Comparative composition 1 | Comparative composition 2 |
|---|---|---|---|---|
| F | Carnauba wax | 9 | 9 | 9 |
| F | Beeswax | 6 | 6 | 6 |
| F | Paraffin wax | 13 | 13 | 13 |
| F | Stearic acid | 2 | 2 | 2 |
| F | Pigment | 8 | 8 | 8 |
| A | Water | q.s. for 100 | q.s. for 100 | q.s. for 100 |
| A | Hydroxyethyl cellulose | 1 | 1 | 1 |
| A | Gum arabic | 4 | 4 | 4 |
| A | Potassium cetyl phosphate (Amphisol K by DSM Nutritional Products) | 4 | 8 | 0 |
| A | Stearoyl Glutamate (Amisoft HS 11 PF by Ajinomoto) | 4 | 0 | 8 |
| A | Preservative system | qs | qs | qs |

These compositions were prepared as follows:

i. Preparation of the Fatty Phase (F)

The various waxes are melted in a 500 mL jacketed heating pan with circulation of hot oil to control the temperature. The mixture is heated to about 96-98° C.

When the waxes are melted and homogenized, the pigments are added then homogenized using a Moritz (rotor stator stirring).

ii. Preparation of the Aqueous Phase (A)

A high-sided 600 ml beaker is used. The amount of water required, preheated by an electric kettle, is stirred slowly in this beaker using a Rayneri blender.

The (co)polymers and then the surfactants are successively added, with continued slow stirring. Between each addition, care should be taken to ensure good dissolution of the compound and homogenization of the medium.

The preservatives are added next.

The aqueous phase is then placed on a water bath (nominal temperature 90-92° C.) until a temperature of 88-90° C. is reached.

iii. Emulsification

When the two phases are at the desired temperature, the aqueous phase is added very slowly into the fatty phase while gradually increasing the stirring. Stirring is maintained for 10 minutes.

iv. Temperature Reduction

After the emulsification, the heating pan is placed on a Rayneri blender equipped with a butterfly paddle, the latter allowing blending and homogenization during the temperature reduction, at low shear. The stirring speed is low so as not to incorporate air bubbles.

Using the oil bath, the temperature is gradually reduced to room temperature (20° C.): by 10° C. steps.

v. End of Formulation

The mascara thus obtained is transferred into a closed jar to prevent it from drying out on contact with air; it is then necessary to wait 24 hours to check the homogeneity of the formulation and the correct dispersion of the pigments.

2/ Protocols and Results

The compositions prepared are then observed under a microscope, then used as make-up, by applying these compositions using a brush.

For comparative composition 1 outside the invention, a very thick texture is observed, that cannot be used as make-up or packaged. What is more, a heterogeneous emulsion with many white spots is observed.

For comparative composition 2 outside the invention, a quite thick and matte texture is observed. The emulsion is irregular.

For the composition according to the invention, a thick, smooth and black texture is observed. What is more the emulsion is fine and uniform. The composition according to the invention is further pleasant to apply. The make-up is uniform. The eyelashes are evenly coated. The composition obtained has good sheen. The pigments are well dispersed. Further, these compositions are stable at 4 and 45° C. for two months.

It is understood that, in the context of the present invention, the weight percentages given for a compound or a family of compounds are always expressed as weight of solids of the compound in question.

Throughout the patent application, the wording "comprising one" or "including one" means "comprising at least one" or "including at least one", unless otherwise specified.

The invention claimed is:

1. A cosmetic composition, comprising:
   an aqueous phase;
   a fatty phase, comprising:
   a polar wax having a melting point of 45° C. or greater, and
   a nonpolar wax having a melting point of 45° C. or greater; and
   an emulsifying system comprising:
   from 2 to 12% by weight relative to the total weight of the composition of a $C_{12}$-$C_{22}$ monoalkyl phosphate, and
   from 3 to 12% by weight relative to the total weight of the composition of an acyl glutamic acid comprising a $C_{12}$-$C_{22}$ acyl chain, a salt thereof, and a mixture thereof,
   wherein
   the polar wax is at least one selected from the group consisting of a silicone wax, an ester wax, a hydrogenated plant oil, a hydrogenated animal oil, beeswax, synthetic beeswax, polyglycerolated beeswax, beeswax esterified with an oxyethylenated group, carnuba wax, candelilla wax, oxypropylenated lanolin wax, rice bran wax, ouricury wax, esparto grass wax, cork fiber wax, sugar cane wax, Japan wax, sumach wax, montan wax, orange wax and laurel wax,
   a total weight of the polar wax and the nonpolar wax is at least 90% by weight of the fatty phase, and the composition is suitable for coating keratin fibres.

2. The composition according to claim 1, wherein the $C_{12}$-$C_{22}$ monoalkyl phosphate is a $C_{16}$-$C_{18}$ monoalkyl phosphate.

3. The composition according to claim 1, wherein the $C_{12}$-$C_{22}$ monoalkyl phosphate is a monocetyl phosphate.

4. The composition according to claim 1, wherein the weight % of the $C_{12}$-$C_{22}$ monoalkyl phosphate is from 3 to 10 weight % relative to the total weight of the composition.

5. The composition according to claim 1, wherein the acyl glutamic acid is at least one selected from the group consisting of lauroyl glutamic acid, myristoyl glutamic acid, palmitoyl glutamic acid, stearoyl glutamic acid, behenoyl glutamic acid, olivoyl glutamic acid, and cocoyl glutamic acid, an alkali metal salt thereof, an alkaline earth metal salt thereof, and an ammonium salt thereof.

6. The composition according to claim 1, wherein the acyl glutamic acid is at least one selected from the group consisting of lauroyl glutamic acid, cocoyl glutamic acid, sodium stearoyl glutamate, potassium lauroyl glutamate, potassium cocoyl glutamate and sodium olivoyl glutamate.

7. The composition according to claim 1, wherein the acyl glutamic acid comprises a monosodium salt of n-stearoyl-L-glutamic acid.

8. The composition according to claim 1, wherein the weight % of the acyl glutamic acid is from 3 to 10% by weight relative to the total weight of the composition.

9. The composition according to claim 1, wherein a weight ratio of the $C_{12}$-$C_{22}$ monoalkyl phosphate to the acyl glutamic acid is from 1/3 to 3/1.

10. The composition according to claim 1, wherein a total wax content is greater than or equal to 10% by weight relative to the total weight of the composition.

11. The composition according to claim 1, wherein the composition comprises at least 20% by weight of the nonpolar wax, relative to the total weight of the wax.

12. The composition according to claim 1, wherein a weight ratio of the $C_{12}$-$C_{22}$ monoalkyl phosphate and the acyl glutamic acid to a total weight of the polar wax and the nonpolar wax is greater than or equal to 1/10.

13. The composition according to claim 1. further comprising a hydrophilic film-forming polymer.

14. The composition according to claim 1, further comprising a dyestuff.

15. A method for coating keratin fibres, the method comprising:
applying the composition according to claim 1 to the keratin fibers.

16. The composition according to claim 1, wherein a weight ratio of the $C_{12}$-$C_{22}$ monoalkyl phosphate to the glutamic acid is from 3/5 to 5/3.

17. The composition according to claim 1, wherein a weight ratio of the $C_{12}$-$C_{22}$ monoalkyl phosphate and the acyl glutamic acid to a total weight of the polar wax and the nonpolar wax is from 1/8 to 1/2.

18. The composition according to claim 1, wherein a weight ratio of the $C_{12}$-$C_{22}$ monoalkyl phosphate and the acyl glutamic acid to a total weight of the polar wax and the nonpolar wax is from 1/4 to 1/3.

* * * * *